United States Patent [19]

Henschler et al.

[11] 4,085,270

[45] Apr. 18, 1978

[54] SYMPATHICOMIMETIC ACYLOXY-PHENYLETHANOLAMINE

[75] Inventors: Dietrich Henschler, Wurzburg; Josef Wagner, Munich; Hans Hampel, Neukeferloh, all of Germany

[73] Assignee: Chemisch-Pharmazeutische Fabrik Adolf Klinge & Co., Munich, Germany

[21] Appl. No.: 297,416

[22] Filed: Oct. 13, 1972

[30] Foreign Application Priority Data

Oct. 19, 1971 Germany .............................. 2152058

[51] Int. Cl.² ............................................. C07C 93/20
[52] U.S. Cl. .................... 560/105; 560/142; 424/309; 424/311
[58] Field of Search ............................ 260/479 R, 477

[56] References Cited
PUBLICATIONS

Zoelss, G. Sci. Pharm 32(2), 76–92 (1964).

Primary Examiner—Paul J. Killos
Attorney, Agent, or Firm—Karl W. Flocks

[57] ABSTRACT

Novel acyloxy-phenylethanolamines, characterized in that the acyloxy group or groups are pivaloyloxy or phenylacetyloxy and having a more prolonged sympaticomimetic action than acyloxy-phenylethanolamines known previously, are described together with a method for their manufacture by reduction of the corresponding acyloxy-phenylketo-N-benzyl amines using hydrogen in an aqueous medium over a noble metal catalyst.

7 Claims, No Drawings

SYMPATHICOMIMETIC ACYLOXY-PHENYLETHANOLAMINE

The subject of the application are new acyl derivatives of sympaticomimetic phenolethanolamines, being acyloxyphenylethanolamines having the general formula I

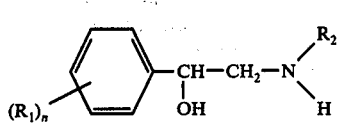

in which $R_1$ represents a pivaloyloxy or phenylacetoxy radical in the 3', 4', 3'4' or 3'5' position and $R_2$ denotes a lower alkyl group with 1-2 C atoms and $n = 1$ or 2.

The uncertain action of the previously known orally administered phenolethanolamines is attributable to transformation processes, especially of an oxidative nature, which can already occur during resorption. These take place preferentially at the phenolic hydroxyl groups and lead rapidly to inactive compounds, especially in the case of compounds with two phenolic hydroxyl radicals as is the case, for example, with adrenalin and its derivatives. As a result of the other rapid metabolisation of the phenolethanolamines in the blood and tissue, an effective concentration — above all for a prolonged period — can therefore frequently not be achieved at the place of action.

It is already known that it is possible to prolong the action by repressing the rate of metabolisation by masking the hydroxyl groups with acyl radicals, especially acetyl radicals, whereby the lipophilic character of the compounds is at the same time increased and hence their resorption properties are improved. After resorption has taken place, however, the acylated compounds hitherto known lose their acyl radicals more or less rapidly through hydrolytic processes in the organism, so that the delayed action cannot be achieved to the desired extent.

It has now been found that to achieve an effect which is as long-lasting as possible only those acyl radicals can be used for masking the compounds which, because of their voluminous bulky structure are only split off with difficulty by the normal esterases of the liver and the blood. According to the invention, trimethylacetic acid (= pivalic acid) and phenylacetic acid are outstandingly suitable for masking the phenolic hydroxyl groups of these sympaticomimetic amine compounds.

To demonstrate the achievable retardation, through the acyl radicals present according to the invention, in the degradation of the new esters by blood enzymes, some results of in vitro experiments are described below. Here, the esterolytic action of human whole blood on the phenylethanolamines acylated in different ways was tested by means of a Warburg apparatus. The corresponding acetic acid ester compounds were used for comparison.

TABLE

Speed of enzymatic splitting of O-acyl-phenylethanolamines in human whole blood *

| | Acyl radical | | |
|---|---|---|---|
| | Acetyl | Phenacetyl | Pivaloyl |
| 3'-O-Acyl-phenylephrin | 90 | 7.2 | 9.2 |
| 3'-O-Acyl-ethylephrin | 56 | 6.0 | 5.5 |
| 4'-O-Acyl-synephrin | 82 | 17.7 | 1 |
| 3'4'-Di-O-acyl-adrenalin | 142 | 31.2 | 0.4 |
| 3'5'-Di-O-acyl-resorcyl-methylaminoethanol | 138 | 7.2 | 0 |

* μl of $CO_2$ liberated/30 μl of whole blood/hour in the Warburg apparatus
Substrate concentration: $10^{-2}$M
Whole blood: 30 μl/3 ml
Buffer: 0.025 M $NaHCO_3$
Gas phase $N_2/CO_2$: 95/5

As is shown by the Table, the compounds substituted, in accordance with the invention, with the bulky acyl radicals are split off several times more slowly than the acetyl group.

The phenolethanolamines masked with pivalic acid or phenylacetic acid are therefore outstandingly suitable for achieving long-lasting sympathotonic effects. This is also confirmed by pharmacological experiments in vivo. After intraduodenol administration to rats the compounds according to the invention show, alongside an improved resorption, also a substantially longer action on the blood pressure than the unprotected (free) phenolethanolamines.

It is thus possible to treat circulatory diseases which require a therapy with a long-lasting sympathotonic effect.

The compounds according to the invention can be manufactured by reacting ketones of the formula II

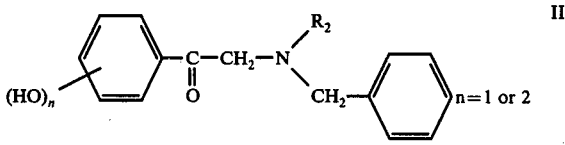

wherein the hydroxyl group or groups are in the 3', 4', 3'4' or 3'5' position and $R_2$ represents a lower alkyl group, with a reactive derivative of pivalic acid or phenylacetic acid, for example an acid halide or the anhydride, after which the benzyl radical is removed by hydrogenation in aqueous solution with hydrogen, using noble metal hydrogenation catalysts, and at the same time the keto group is reduced to the alcohol.

The manufacture of O-acetyl and O-propionyl derivatives of phenylephrin, synephrin, adrenalin and aludrin is known (Bretschneider, Monatshefte fuer Chemie: 76, 355, 368; 77, 385 (1947); 78, 71, 82, 117 (1948)). O-Acylated derivatives of 3'5'-di-hydroxyphenylethanolamine with aliphatic optionally branched acid radicals, preferably with 2-6 C atoms, have also been described (Messrs. Lentia: DAS No. 1,257,791, filed on June 23, 1961; Austrian Pat. No. 226,219, filed on June 21, 1961). The starting substances differ from the compounds claimed through the primary amino group. Finally, phenolalkanolamines acrylated at the amino group are also known (Messrs. Diwag: DOS 1,543,522, filed on July 14, 1966; DOS No. 1,593,828, filed on May 16, 1967; DOS No. 1,593,834 filed on May 26, 1967.

The manufacture of the compounds according to the invention is described in more detail in the examples which follow.

EXAMPLE 1

30 parts of 1-(4'-hydroxyphenyl)-2-(N-benzylaminomethyl)-ethan-1-one are mixed with 100 parts of pyridine and 30 parts of pivalic anhydride and dissolved whilst warming. After heating for 1 hour under reflux, the acylation is complete. After concentrating the reaction solution, the product is precipitated from acetone/ether.

Yield: 96.4% of 1-(4'-pivaloyloxyphenyl)-2-(N-benzylaminomethyl)-ethan-1-one.

2 parts of palladium/charcoal (10 percent strength) are pre-hydrogenated in water, thereafter 30 parts of 1-(4'-pivaloyloxyphenyl)-2-(N-benzylaminomethyl)-ethan-1-one, dissolved in a 20-fold amount of water, are added dropwise at room temperature and hydrogenation is carried out until 1 mol of hydrogen has been taken up. After filtering off the catalyst, 2 parts of palladium/charcoal are again added and hydrogenation is carried out until a further mol of hydrogen has been taken up. The catalyst is separated off and after removal of the solvent the hydrogenation product is re-precipitated from acetic acid ethyl ester/ether and from acetone until it is pure according to thin layer chromatography.

Yield: 35.4% of 1-(4'-pivaloyloxyphenyl)-2-methylaminoethanol-1. Hydrochloride. Melting point 190°-192°, $R_f$ 0.8 in chloroform/methanol/water (59/33/8).

EXAMPLE 2

25 parts of 1-(3'-hydroxyphenyl)-2-(N-benzylaminoethanol)-ethan-1-one are mixed with 25 parts of phenylacetic acid and 100 parts of phenylacetic acid chloride and dissolved whilst warming. After 20 minutes' heating under reflux, the acylation is complete. The crude product separates out on adding petroleum ether to the cooled reaction solution, and is obtained in a pure form, according to thin layer chromatography, from acetone/ether.

Yield: 69.5% of 1-(3'-phenylacetoxyphenyl)-2-(N-benzylaminoethanol)-ethan-1-one.

5 parts palladium/charcoal (10 percent strength) are pre-hydrogenated in water, thereafter 24 parts of 1-(3-phenylacetoxyphenyl)-2-(N-benzylaminoethyl)-ethan-1-one, dissolved in a 10-fold amount of water, are added dropwise at room temperature and the mixture is hydrogenated until 2 mols of hydrogen have been taken up. The catalyst is separated off and after removal of the solvent the hydrogenation product is reprecipitated from acetone/ether at 0° C until it is pure according to thin layer chromatography.

Yield: 49.5% of 1-(3'-phenylacetoxyphenyl)-2-ethylaminoethanol-1. Hydrochloride. Melting point 110°-112°, $R_f$ 0.6 in chloroform/methanol/water (59/33/8), soluble in water and ethanol.

EXAMPLE 3

3 parts of palladium/charcoal (10 percent strength) are pre-hydrogenated in water, thereafter 10 parts of 1-(3'-pivaloyloxyphenyl)-2-(N-benzylaminoethyl)-ethan-1-one, dissolved in a 10-fold amount of water, are added dropwise at room temperature and hydrogenation is carried out until 1 mol of hydrogen has been taken up. After filtering off the catalyst, a further 3 parts of palladium/charcoal are added and hydrogenation is carried out until a further mol of hydrogen has been taken up. The catalyst is separated off and after removal of the solvent the hydrogenation product is re-precipitated from acetone/petroleum ether and from methanol/ether until it is pure according to thin layer chromatography.

Yield: 38.8% of 1-(3'-pivaloyloxyphenyl)-2-ethylaminoethanol-1. Hydrochloride, melting point 208°-209°, $R_f$ 0.65 in chloroform/methanol/water (59/33/8). Pivaloyl content: calculated 28.3%, found 25.6%, soluble in water and ethanol.

EXAMPLE 4

1 part of palladium/charcoal (10 percent strength) is pre-hydrogenated in water, thereafter 8 parts of 1-(3'-pivaloyloxyphenyl)-2-(N-benzylaminomethyl)-ethan-1-one, dissolved in a 12-fold amount of water, are added dropwise at room temperature and hydrogenation is carried out until 2 mols of hydrogen have been taken up. The catalyst is separated off and after removal of the solvent the hydrogenation product is reprecipitated from acetic acid ethyl ester/ether and from chloroform/ether at 0° C until it is pure according to thin layer chromatography.

Yield: 35.5% of 1-(3'-pivaloyloxyphenyl)-2-methylaminoethanol-1 hydrochloride. Melting point 155°, $R_f$ 0.5 in chloroform/methanol/water (59/33/8). Pivaloyl content: calculated 29.6%, found 28.7%, soluble in water and ethanol.

EXAMPLE 5

2 parts of palladium/charcoal (10 percent strength) are pre-hydrogenated in water, thereafter 15 parts of 1-(3',4'-dipivaloyloxyphenyl)-2-(N-benzylaminomethyl)-ethan-1-one, dissolved in a 12-fold amount of water, are added dropwise at room temperature and hydrogenation is carried out until 1 mol of hydrogen has been taken up. After filtering off the catalyst, a further 2 parts of palladium/charcoal are added and hydrogenation is carried out until a further mol of hydrogen has been taken up. The catalyst is separated off and after removal of the solvent the hydrogenation product is reprecipitated from ether/petroleum ether and from acetic acid ethyl ester until it is pure according to thin layer chromatography.

Yield: 71.9% of 1-(3',4'-dipivaloyloxyphenyl)-2-methylamino-ethanol-1. Hydrochloride. Melting point 158°-159°, $R_f$ 0.8 in chloroform/methanol/$H_2O$ (59/33/8), soluble in water and ethanol.

EXAMPLE 6

1 part of palladium/charcoal (10 percent strength) is pre-hydrogenated in water, thereafter 7 parts of 1-(3'-phenylacetoxyphenyl)-2-(N-benzylaminomethyl)-ethan-1-one, dissolved in a 12-fold amount of water, are added dropwise at room temperature and hydrogenation is carried out until 2 mols of hydrogen have been taken up. The catalyst is separated off and after removal of the solvent the hydrogenation product is re-precipitated from acetone/ether until it is pure according to thin layer chromatography.

Yield: 55% of 1-(3'-phenylacetoxyphenyl)-2-methylaminoethanol-1. Hydrochloride; $R_f$ 0.5 in chloroform/methanol/water (59/33/8), soluble in water and ethanol.

EXAMPLE 7

1 part of palladium/charcoal (10 percent strength) is pre-hydrogenated in acetone at 35°-40°, thereafter 1-(4'-phenylacetoxyphenyl)-2-(N-benzylaminomethyl)-ethan-1-one, dissolved in acetone, is added dropwise at 35° and hydrogenation is carried out until 1 mol of hydrogen has been taken up. The substance which has precipitated is filtered off together with the catalyst and separated from the catalyst by means of methanol. Reprecipitation from the methanol solution, by means of ether, and subsequent reprecipitation from methanol/ether leads to 1-(4'-phenylacetoxyphenyl)-2-methylamino-ethan-1-one which is pure according to thin layer chromatography.

1.5 parts of palladium/charcoal (10 percent strength) are pre-hydrogenated in water, thereafter 5 parts of 1-(4'-phenylacetoxyphenyl)-2-methylamino-ethan-1-one, dissolved in a 20-fold amount of water, are added dropwise at room temperature and hydrogenation is carried out until 1 mol of hydrogen has been taken up. The catalyst is separated off and after removal of the solvent the hydrogenation product is reprecipitated from ether and from methanol/ether until it is pure according to thin layer chromatography.

Yield: 49.6% of 1-(4'-phenlacetoxyphenyl)-2-methylaminoethanol-1. Hydrochloride. Melting point: 147°–149°, $R_f$ 0.8 in chloroform/methanol/water (59/33/8), soluble in water and ethanol.

EXAMPLE 8

2 parts of palladium/charcoal (10 percent strength) are pre-hydrogenated in water, thereafter 5 parts of 1-(3',5'-dipivaloyloxyphenyl)-2-(N-benzylaminomethyl)-ethan-1-one, dissolved in a 20-fold amount of water, are added dropwise at room temperature and hydrogenation is carried out until 2 mols of hydrogen have been taken up. The catalyst is separated off and after removal of the solvent the hydrogenation product is reprecipitated from cold acetone/petroleum ether until it is pure according to thin layer chromatography.

Yield: 43.7% of 1-(3',5'-dipivaloyloxyphenyl)-2-methylaminoethanol-1. Hydrochloride. Melting point 131°–135°, $R_f$ 0.8 in chloroform/methanol/water (59/33/8), soluble in water and ethanol.

EXAMPLE 9

2 parts of palladium/charcoal (10 percent strength) are pre-hydrogenated in 10 parts of water at 45° C, thereafter 4 parts of (3',4'-diphenylacetoxyphenyl)-2-(N-benzylmethylamino)-ethan-1-one, dissolved in 30 parts of acetone are added dropwise at 45° C and hydrogenation is carried out until 2 mols of hydrogen have been taken up. The catalyst is separated off and after removal of the solvent the hydrogenation product is reprecipitated from acetone/ether and methanol/ether until it is pure according to thin layer chromatography.

Yield: 25% of 1-(3',4'-diphenylacetoxyphenyl)-2-methylamino-ethanol-1. Hydrochloride. Melting point: 173°–176°, $R_f$ 0.5 in chloroform/methanol/water (59/33/8), soluble in water and ethanol.

EXAMPLE 10

2 parts of palladium/charcoal (10 percent strength) are pre-hydrogenated in 20 parts of water at 45°, thereafter 5 parts of 1-(3',5'-diphenylacetoxyphenyl)-2-(N-benzylmethylamino)-ethan-1-one, dissolved in 40 parts of acetone are added dropwise at 45° C and hydrogenation is carried out until 2 mols of hydrogen have been taken up. The catalyst is separated off and after removal of the solvent the hydrogenation product is reprecipitated from acetic acid ethyl ester/ether and from methanol/ether until it is pure according to thin layer chromatography.

Yield: 30.8% of 1-(3',5'-diphenylacetoxyphenyl)-2-methylamino-ethanol-1. Hydrochloride. Melting point: 117°–118°, $R_f$ 0.75 in chloroform/methanol/water (59/33/8), soluble in water and ethanol.

The following further compounds can be manufactured in the same manner, using the method described: 1-(4'-pivaloyloxyphenyl)-2-ethylamino-ethanol-1; 1-(4'-phenylacetoxyphenyl)-2-ethylamino-ethanol-1; 1-(3',4'-pivaloyloxyphenyl)-2-ethylamino-ethanol-1; 1-(3',4'-phenylacetoxyphenyl)-2-ethylamino-ethanol-1; 1-(3',5'-pivaloyloxyphenyl)-2-ethylamino-ethanol-1 and 1-(3'5'-phenacetyloxyphenyl)-2-ethylamino-ethanol-1.

We claim:

1. Mono-acyloxy-phenylethanolamines having the general formula:

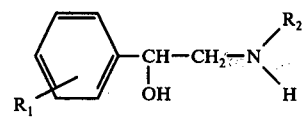

wherein $R_1$ is pivaloyloxy or phenylacetyloxy in the 3' or 4' position, and $R_2$ is methyl or ethyl.

2. A methyl of synthesising an acyloxy-phenylethanolamine which method comprises reducing a compound having the general formula:

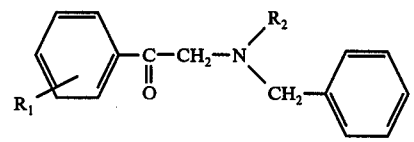

wherein $R_1$, $R_2$ are as defined in claim 1, with hydrogen in an aqueous medium in the presence of a noble metal hydrogenation catalyst.

3. A method as claimed in claim 2 wherein the noble metal hydrogenation catalyst is palladised charcoal.

4. A method as claimed in claim 2 including the preliminary step of reacting a compound having the general formula:

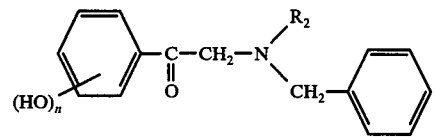

wherein $R_2$ is lower alkyl and $n$ is either 1 or 2 such that the hydroxy substituent or substituents are in the 3', 4', 3'4' or 3'5' positions, with a reactive derivative of pivaloyl or phenylacetic acid to form an intermediate compound having the general formula:

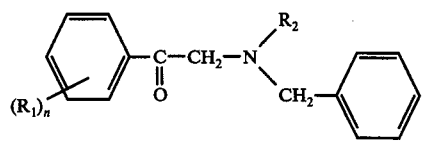

wherein $R_1$ is pivaloyloxy or phenylacetyloxy, $R_2$ is lower alkyl and $n$ is either 1 or 2 such that the substituent or substituents R are in the 3', 4', 3'4' or 3'5' positions.

5. A compound of the formula

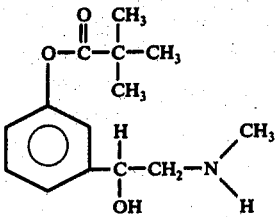

or the hydrochloride thereof.

6. A compound according to claim 5 wherein the compound is 3-pivaloxy - $\alpha$ - [(methylamino)methyl]-benzyl alcohol.

7. 1-(3'-pivaloyloxyphenyl)-2-methylamino-ethanol-1 hydrochloride.

* * * * *

UNITED STATES PATENT OFFICE
CERTIFICATE OF CORRECTION

Patent No. 4,085,270  Dated  April 18, 1978

Inventor(s) Dietrich HENSCHLER, Josef WAGNER and Hans HAMPEL

It is certified that error appears in the above-identified patent and that said Letters Patent are hereby corrected as shown below:

Title Page, [73] Assignee:, should read as follows:

[73] Assignee: KLINGE PHARMA GMBH & CO.

*Signed and Sealed this*

*Twenty-sixth* Day of *February 1980*

[SEAL]

*Attest:*

SIDNEY A. DIAMOND

*Attesting Officer*  *Commissioner of Patents and Trademarks*